(12) United States Patent
Chin et al.

(10) Patent No.: US 10,807,063 B1
(45) Date of Patent: Oct. 20, 2020

(54) DEVICE AND METHOD FOR CONTINUOUSLY MANUFACTURING ACRYLATE COMPOUND

(71) Applicant: INDUSTRIAL TECHNOLOGY RESEARCH INSTITUTE, Hsinchu (TW)

(72) Inventors: Chih-Lung Chin, Hsinchu (TW); Chang-Hung Wu, Taoyuan (TW); Shih-Hsien Liu, Jhubei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 16/731,490

(22) Filed: Dec. 31, 2019

(51) Int. Cl.
*B01J 19/00* (2006.01)
*B01J 19/24* (2006.01)
(Continued)

(52) U.S. Cl.
CPC ......... *B01J 19/0093* (2013.01); *B01J 19/002* (2013.01); *C07C 67/08* (2013.01);
(Continued)

(58) Field of Classification Search
CPC ...... B01J 19/00; B01J 19/0006; B01J 19/002; B01J 19/0093; B01J 19/24; B01J 2219/00; B01J 2219/00002; B01J 2219/00027; B01J 2219/00033; B01J 2219/0004; B01J 2219/00049; B01J 2219/00245;
(Continued)

(56) References Cited

U.S. PATENT DOCUMENTS

| 4,059,721 A | 11/1977 | Rosenkranz et al. |
| 4,329,492 A | 5/1982 | Andoh et al. |

(Continued)

FOREIGN PATENT DOCUMENTS

| CN | 102491896 A | 3/2014 |
| CN | 103030558 A | 5/2017 |

(Continued)

OTHER PUBLICATIONS

Asano et al., "Improvement in the Yield of an Equilibrium Esterification Reaction Using a Microreactor for Water Separation", Journal of Chemical Engineering of Japan, vol. 46, No. 4, 2013, pp. 313-318 (7 pages).

(Continued)

*Primary Examiner* — Natasha E Young
(74) *Attorney, Agent, or Firm* — Birch, Stewart, Kolasch & Birch, LLP (57) ABSTRACT

A device for continuously manufacturing acrylate compound and a method for continuously manufacturing acrylate compound are provided. The device for continuously manufacturing acrylate compound includes a reaction system, a feed tank and a collection tank. The feed tank connects to the inlet port of the reaction system, in order to introduce an alcohol compound and acrylic acid compound into the reaction system. The collection tank connects to the outlet port of the reaction system, in order to collect the acrylate compound. In particular, the reaction system includes at least two reaction units, an inlet port and an outlet port, wherein each reaction unit includes a microreactor and a centrifugal element.

20 Claims, 6 Drawing Sheets

(51) Int. Cl.
*C07C 67/08* (2006.01)
*C07C 67/48* (2006.01)
*C07C 69/602* (2006.01)

(52) U.S. Cl.
CPC ............... *B01J 2219/0004* (2013.01); *B01J 2219/00033* (2013.01); *B01J 2219/00254* (2013.01); *B01J 2219/00272* (2013.01); *B01J 2219/00891* (2013.01); *B01J 2219/00905* (2013.01); *C07C 67/48* (2013.01); *C07C 69/602* (2013.01)

(58) Field of Classification Search
CPC .... B01J 2219/00254; B01J 2219/00272; B01J 2219/00781; B01J 2219/00891; B01J 2219/00905; C07C 67/00; C07C 67/08; C07C 67/48; C07C 69/00; C07C 69/52; C07C 69/602
See application file for complete search history.

(56) References Cited

U.S. PATENT DOCUMENTS

| | | | |
|---|---|---|---|
| 4,435,594 A | 3/1984 | Matsumura et al. | |
| 4,464,229 A | 8/1984 | Sato et al. | |
| 5,659,072 A | 8/1997 | Bessalem et al. | |
| 6,175,037 B1 | 1/2001 | Tweedy | |
| 7,052,743 B2 | 5/2006 | Welter et al. | |
| 7,723,439 B2 | 5/2010 | Furuta et al. | |
| 8,715,528 B2 | 5/2014 | Chen et al. | |
| 8,940,925 B2 | 1/2015 | Paul et al. | |
| 9,682,916 B2 | 6/2017 | Ciceron | |
| 9,975,842 B2 | 5/2018 | Moreliere et al. | |
| 10,035,956 B2 | 7/2018 | Chin et al. | |
| 2002/0099165 A1 | 7/2002 | Nagar et al. | |
| 2004/0019235 A1 | 1/2004 | Martin et al. | |
| 2012/0271064 A1* | 10/2012 | Henninger | C07C 69/54 560/224 |
| 2013/0035504 A1 | 2/2013 | Baro et al. | |
| 2014/0357889 A1 | 12/2014 | McCarthy et al. | |
| 2017/0267624 A1 | 9/2017 | Moreliere et al. | |
| 2017/0327626 A1 | 11/2017 | Roller et al. | |
| 2018/0155481 A1 | 6/2018 | Share et al. | |
| 2019/0233655 A1 | 8/2019 | Kimpel et al. | |

FOREIGN PATENT DOCUMENTS

| | | |
|---|---|---|
| CN | 106748760 A | 5/2017 |
| CN | 106536473 A | 5/2019 |
| TW | I410424 B | 10/2013 |
| TW | I414527 B | 11/2013 |
| TW | I443180 B | 7/2014 |
| TW | I480635 B | 4/2015 |
| TW | I641589 B | 11/2018 |

OTHER PUBLICATIONS

Chandane et al., "Enhancement of esterfication conversion using pervaporation membrane reactor", ScienceDirect, Resource-Efficient Technologies 2, 2016 (available online Nov. 10, 2016), pp. S47-S52 (6 pages).

Sert et al., "Enhancement of Conversion using Ceramic Membrane in Esterification of Acrylic Acid with Butanol", Journal of Polytechnic; vol. 20, No. 2, 2017, pp. 437-440 (4 pages).

* cited by examiner

DEVICE AND METHOD FOR CONTINUOUSLY MANUFACTURING ACRYLATE COMPOUND

TECHNICAL FIELD

The present disclosure relates to a device and a method for continuously manufacturing acrylate compound.

BACKGROUND

The esterification reaction is the most fundamental and important reaction of organic synthesis and the reaction product is widely used in the industry. The predominant industrial production process for the direct esterification of hydroxy compounds with acrylic acid is based on the use of volatile organic solvents as a liquid reaction medium. This is also known as a solvent operation.

Since the use of organic solvents is being regulated to increasing degrees due to environmental protection considerations, there is an increasing need for an alternative production process, in which the direct esterification of acrylic acid with hydroxy compounds may be carried out in acrylic acid itself as the liquid reaction medium, without the need to use volatile organic solvents (also known as a neat reaction). A conventional batch reactor, however, is not suitable to be used as a reactor for performing a neat reaction of esterification, since it may cause local overheating and lead to danger due to uneven distribution of reactants.

In view of the fact that the esterification reaction is completed to achieve a reversible thermodynamic equilibrium, the water produced (i.e. the byproduct) should be withdrawn in order to enhance the conversion. Conventional methods of employing a batch reactor for performing esterification use a significant amount of azeotropic entrainer in order to remove the water produced as a byproduct of the reaction through azeotropic distillation. However, the azeotropic entrainer (such as Benzene, toluene, xylene, or cyclohexane), known as volatile organic compounds, is expensive and exhibits high toxicity.

A persistent aim of the chemical industry is to constantly improve and control chemical reactions. Greater control over reactions may lead to, for example, environment-friendly processes, improvements in safety, increases in reaction product yield and/or purity of highly reactive intermediate products. Therefore, there is a need to develop a novel method for preparing acrylate in order to solve the above problems.

SUMMARY

According to embodiments of the disclosure, the disclosure provides a device for continuously manufacturing acrylate compound. The device for continuously manufacturing acrylate compound can include a reaction system, a feed tank, and a collection tank. The reaction system can include at least two reaction unit, an inlet port, and an outlet port. The feed tank connects to the inlet port of the reaction system, in order to introduce an alcohol compound and acrylic acid compound into the reaction system. The collection tank connects to the outlet port of the reaction system, in order to collect the acrylate compound. In addition, each reaction unit can include a microreactor and a centrifugal element.

According to embodiments of the disclosure, the disclosure provides a method for continuously manufacturing acrylate compound. The method for continuously manufacturing acrylate compound includes (A) providing a composition into a microreactor to undergo esterification, obtaining an acrylate-compound-containing solution with a first-stage alcohol compound conversion, and wherein the composition comprises an alcohol compound and an acrylic acid compound; (B) introducing the acrylate-compound-containing solution into a centrifugal element in order to remove water from the acrylate-compound-containing solution, obtaining a dehydration solution; and (C) introducing the dehydration solution into another microreactor, obtaining an acrylate-compound-containing solution with a second-stage alcohol compound conversion.

BRIEF DESCRIPTION OF THE DRAWINGS

A detailed description is given in the following embodiments with reference to the accompanying drawings. It should be emphasized that many features are not drawn to scale according to standard practice in the industry. In fact, the dimensions of the various components may be arbitrarily increased or decreased for clarity of discussion.

DETAILED DESCRIPTION

The device and method for continuously manufacturing acrylate compound of the disclosure are described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. In addition, the drawings of different embodiments may use like and/or corresponding numerals to denote like and/or corresponding elements in order to clearly describe the present disclosure. However, the use of like and/or corresponding numerals in the drawings of different embodiments does not suggest any correlation between different embodiments.

The use of ordinal terms such as "first", "second", "third", etc., in the disclosure to modify an element does not by itself connote any priority, precedence, or order of one claim element over another or the temporal order in which it is formed, but are used merely as labels to distinguish one claim element having a certain name from another element having the same name (but for use of the ordinal term) to distinguish the claim elements.

The disclosure provides a device for manufacturing acrylate compound and a method for manufacturing acrylate compound. The method for manufacturing acrylate compound of the disclosure is a continuous process, and the device for manufacturing acrylate compound can be used in the method for continuously manufacturing acrylate compound.

The disclosure provides a device for continuously manufacturing acrylate compound. Since the device for continuously manufacturing acrylate compound of the disclosure employs a microreactor (such as a microreactor having microtubes) and a centrifugal element, a process of continuous esterification, which is a neat reaction, with high conversion can be performed.

In addition, since the device for continuously manufacturing acrylate compound of the disclosure employs a microreactor having microtubes, massive production may be achieved easily and safely by increasing the microtubes of the microreactor. In comparison with a conventional batch reactor, the process of the method for preparing acrylate of the disclosure is stable and safe when the esterification is enlarged, and the reaction time of esterification can be shortened greatly. Furthermore, since the device for continuously manufacturing acrylate compound of the disclosure further includes centrifugal element, the centrifugal element can remove water from the acrylate-compound-containing solution supplied by the microreactor and introduces the dehydration solution into the next microreactor. As a result, the whole conversion of the esterification can be improved.

Figure 1:
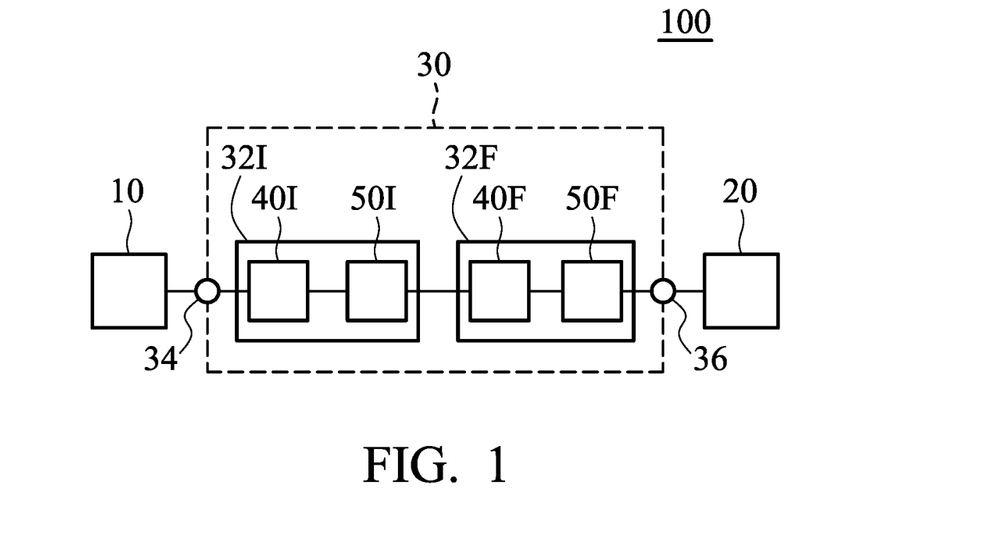
FIG. 1 is a schematic diagram of the device for continuously manufacturing acrylate compound according to an embodiment of the disclosure.

FIG. 1 is a schematic diagram of the device for continuously manufacturing acrylate compound according to an embodiment of the disclosure. As shown in FIG. 1, the device for continuously manufacturing acrylate compound 100 can include a feed tank 10, a collection tank 20, and a reaction system 30. The reaction system 30 has at least two reaction units. In addition, the reaction system 30 has an inlet port 34 and an outlet port 36, wherein the feed tank 10 connects to the inlet port 34 of the reaction system 30, and the collection tank 20 connects to the outlet port 36 of the reaction system 30. The feed tank can introduce the alcohol compound and acrylic acid compound into the reaction system 30, and the collection tank 20 can collect the acrylate compound.

As shown in FIG. 1, the reaction system 30 has two reaction units, i.e. an initial reaction unit 32I and a final reaction unit 32F. Herein, the initial reaction unit 32I and final reaction unit 32F can be connected in series. In the device for continuously manufacturing acrylate compound of the disclosure, each reaction unit has a microreactor and a centrifugal element. As shown in FIG. 1, the initial reaction unit 32I has a microreactor 40I and a centrifugal element 50I, and the final reaction unit 32F has a microreactor 40F and a centrifugal element 50F. According to embodiments of the disclosure, the alcohol compound is reacted with the acrylic acid compound in the microreactor to undergo the esterification. The centrifugal element can remove water from the acrylate-compound-containing solution, which is supplied by the microreactor, obtaining a dehydration solution.

According to embodiments of the disclosure, the centrifugal element can be an electric centrifuge. In addition, according to embodiments of the disclosure, the centrifugal element can also be a mechanical centrifuge, a hydraulic centrifuge, or a pneumatic centrifuge, in order to perform a centrifugation in the absence of electricity.

According to embodiments of the disclosure, the microreactor can include at least one microtube, wherein the inner diameter of the microtube can be from 0.05 mm to 6 mm, such as about 0.5 mm, 1.0 mm, 1.5 mm, 2 mm, or 3 mm.

As shown in FIG. 1, the microreactor 40I of the initial reaction unit 32I connects to the inlet port 34 of the reaction system 30. Therefore, the feed tank 10 can introduce the alcohol compound and the acrylic acid compound into the microreactor 40I of the initial reaction unit 32I via the inlet port 34. In addition, the centrifugal element 50F of the final reaction unit 32F connects to the outlet port 36 of the reaction system 30, and thus the dehydration solution supplied by the centrifugal element 50F can be introduced into the collection tank via the outlet port 36. As shown in FIG. 1, in each reaction unit (such as initial reaction unit 32I), the microreactor (such as the microreactor 40I of the initial reaction unit 32I) connects to the centrifugal element (such as the centrifugal element 50I of the initial reaction unit 32I). As a result, the acrylate-compound-containing solution supplied by the microreactor 40I can be introduced into the centrifugal element 50I (in the same reaction unit) and then subjected to dehydration.

In order to achieve the purpose for continuously manufacturing acrylate compound and enhance the alcohol compound conversion (i.e. the yield of the acrylate compound), in any two adjacent reaction units, the centrifugal element of a previous reaction unit can connect to the microreactor of the next reaction unit. In the disclosure, the reaction unit, which is closer to the feed tank 10, of the two adjacent reaction units is defined as the "previous reaction unit", and the other reaction unit, which is closer to the collection tank 20, of the two adjacent reaction units is defined as the "next reaction unit."

As shown in FIG. 1, the initial reaction unit 32I is positioned adjacent to the final reaction unit 32F, and thus the centrifugal element 40I of the initial reaction unit 32I can connect to the microreactor 40F of the final reaction unit 32F. As a result, the dehydration solution supplied by the centrifugal element 40I can be introduced into the microreactor 40F. Since water is removed from the solution by centrifugal element 50I before introducing into the microreactor 40F, the whole alcohol compound conversion can be improved after performing the esterification by the microreactor 40F.

Herein, the whole alcohol compound conversion ($T_{all}$) refers to the percentage that the alcohol compound (introduced from the inlet port to the reaction system) transforms to other compounds. The equation for calculating the whole alcohol compound conversion ($T_{all}$) is represented as $T_{all} = (1-M')/M° \times 100\%$, wherein M' is the number of moles of reaction residue of the alcohol compound (in the collection tank), and M° is the number of moles of the alcohol compound introduced into the reaction system.

In addition, when continuously manufacturing acrylate compound by the device 100 as shown in FIG. 1, the alcohol compound (supplied by the feed tank 10) is reacted with the acrylic acid compound (supplied by the feed tank 10) in the microreactor 40I to undergo a first esterification, obtaining an acrylate-compound-containing solution with a first-stage alcohol compound conversion ($T_1$). Next, the acrylate-compound-containing solution with the first-stage alcohol compound conversion ($T_1$) is introduced into the centrifugal element 50I to be subjected to a first dehydration, obtaining a dehydration solution. Since the centrifugal element 501 connects to the microreactor 40F, the dehydration solution is introduced into the microreactor 40F to be subjected to a second esterification, obtaining an acrylate-compound-containing solution with a second-stage alcohol compound conversion ($T_2$). Since water produced in the first esterification is removed before performing the second esterification, the equilibrium of the reaction is shifted to the product (acrylate compound) side. As a result, the second-stage alcohol compound conversion ($T_2$) can be improved (i.e. the second-stage alcohol compound conversion ($T_2$) is greater than the first-stage alcohol compound conversion ($T_1$)). The equation for calculating the $n^{th}$-stage alcohol compound conversion ($T_n$) is represented as $T_n = (1-C')/Co \times 100\%$, wherein n is the number of the esterification performed in various microreactors, C' is the signal intensity of the alcohol compound in the result obtained by the nth esterification, and Co is the signal intensity of the alcohol compound in the solution introduced into the reaction system. The signal intensity can be determined by a method such as mass spectrometry (MS), high performance liquid chromatography (HPLC), gas chromatography (GC), or gas chromatography-mass spectrometry (GC-MS). According to embodiments of the disclosure, when the alcohol compound is a monohydric alcohol compound, the first-stage alcohol compound conversion ($T_1$) can be about 50% to 60%, and the second-stage alcohol compound conversion ($T_2$) can be about 80% to 96%. According to embodiments of the disclosure, the device for continuously manufacturing acrylate compound having two reaction units is suitable to be used in the process for transferring a monohydric alcohol compound to an acrylate compound.

Figure 2:
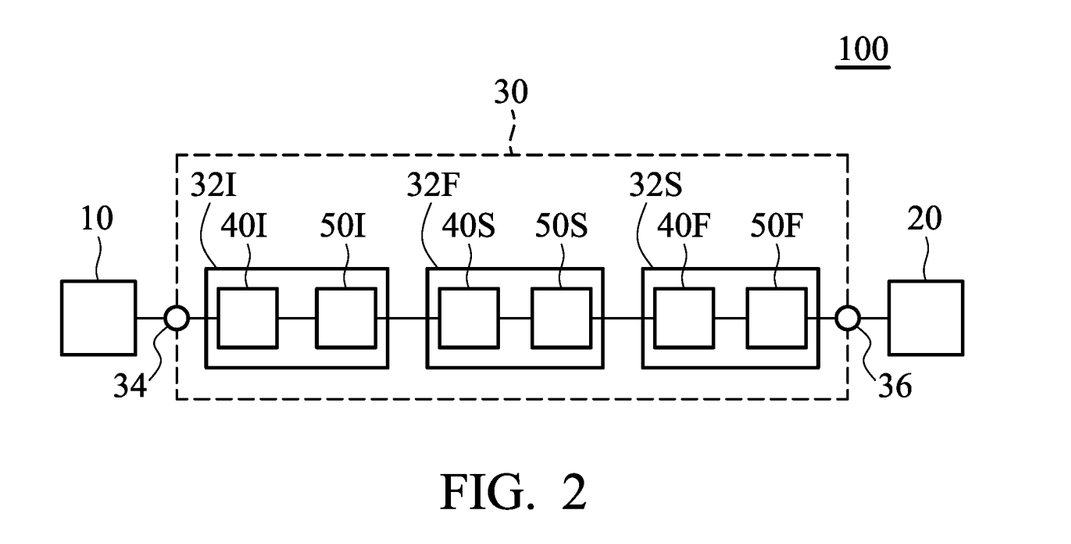
FIG. 2 is schematic diagram of the device for continuously manufacturing acrylate compound, which has three reaction units, according to an embodiment of the disclosure.

According to embodiments of the disclosure, in order to achieve the purpose for continuously manufacturing acrylate compound and enhance the whole alcohol compound (such as dihydric alcohol or trihydric alcohol) conversion (i.e. the yield of the acrylate compound), the reaction system 30 of the device for continuously manufacturing acrylate compound can include more than two reaction units (such as three, four, five, or six reaction units), and the more than two reaction units are connected in series. In addition, in any two adjacent reaction units, the centrifugal element of a previous reaction unit connects to the microreactor of the next reaction unit. As shown in FIG. 2, the device 100 for continuously manufacturing acrylate compound of the disclosure has three reaction units (i.e. the initial reaction unit 32I, the second reaction unit 32S, and the final reaction unit 32F). As shown in FIG. 2, the second reaction unit 32S is positioned between the initial reaction unit 32I and the final reaction unit 32F (i.e. the initial reaction unit 32I is the previous reaction unit regarding to the second reaction unit 32S, and the final reaction unit 32F is the next reaction unit regarding to the second reaction unit 32S). In the second reaction unit 32S, the microreactor 40S of the second reaction unit 32S connects to the centrifugal element 50S; the microreactor 40S of the second reaction unit 32S connects to the centrifugal element of the previous reaction unit (i.e. the centrifugal element 501 of the initial reaction unit 32I); and, the centrifugal element 50S of the second reaction unit 32S connects to the microreactor of the next reaction unit (i.e. the microreactor 40F of the final reaction unit 32F). As a result, when continuously manufacturing acrylate compound via the device 100 of FIG. 2, there are three esterifications performed, and each esterification is performed in the absence of water (or in the substantial absence of water). As a result, the whole alcohol compound (such as dihydric alcohol or trihydric alcohol) conversion can be improved.

In addition, according to embodiments of the disclosure, the final reaction unit 32F may not include a centrifugal element (i.e. the final reaction unit 32F is consisted of the microreactor 40F).

Figure 3:
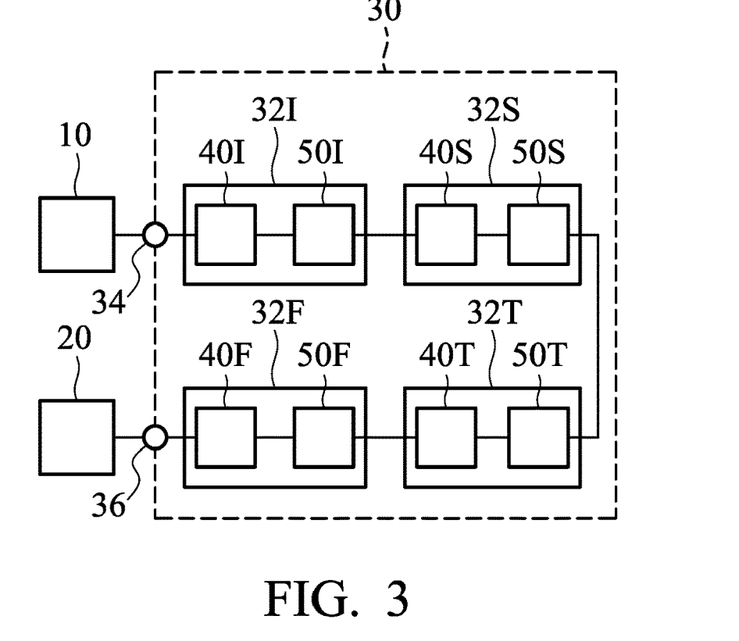
FIG. 3 is schematic diagram of the device for continuously manufacturing acrylate compound, which has four reaction units, according to an embodiment of the disclosure.

According to embodiments of the disclosure, As shown in FIG. 3, the device for continuously manufacturing acrylate compound of the disclosure 100 can include four reaction units, i.e. the initial reaction unit 32I, the second reaction unit 32S, the third reaction unit 32T and the final reaction unit 32F.

Figure 4:
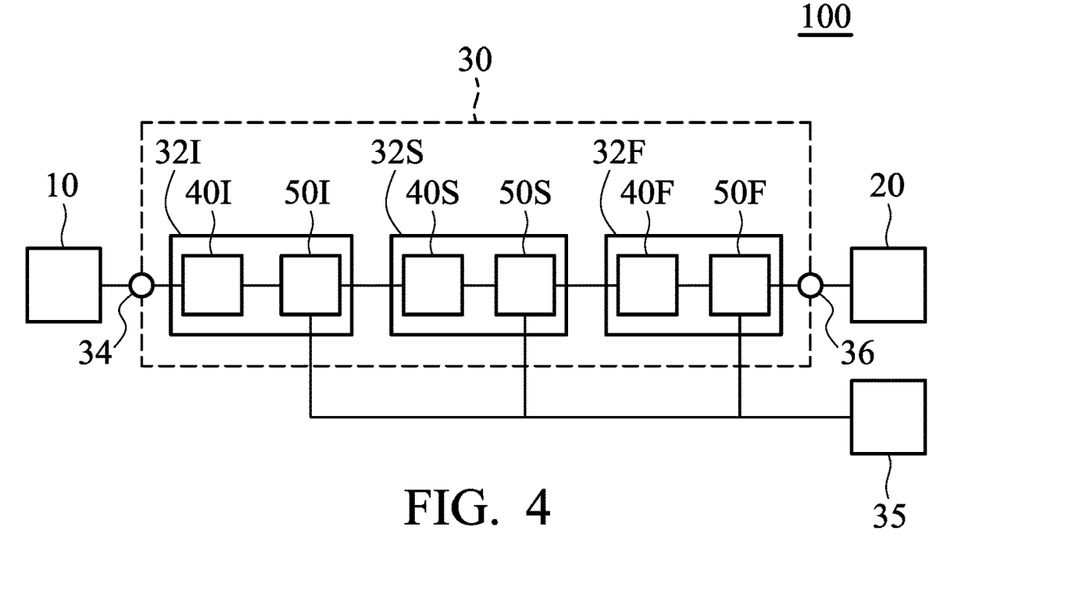
FIG. 4 is schematic diagram of the device for continuously manufacturing acrylate compound, which has a recovery tank, according to an embodiment of the disclosure.

According to embodiments of the disclosure, the device for continuously manufacturing acrylate compound of the disclosure 100 can further include a recovery tank 35, as shown in FIG. 4. The reaction system 30 can have three reaction units, wherein the centrifugal element of each reaction unit can connect to the recovery tank 35. As a result, the water removed via the centrifugal element may be collected by the recovery tank.

According to embodiments of the disclosure, in the device for continuously manufacturing acrylate compound of the disclosure, the reaction system can further include at least one first control element disposed between the two adjacent reaction units.

Figure 5:
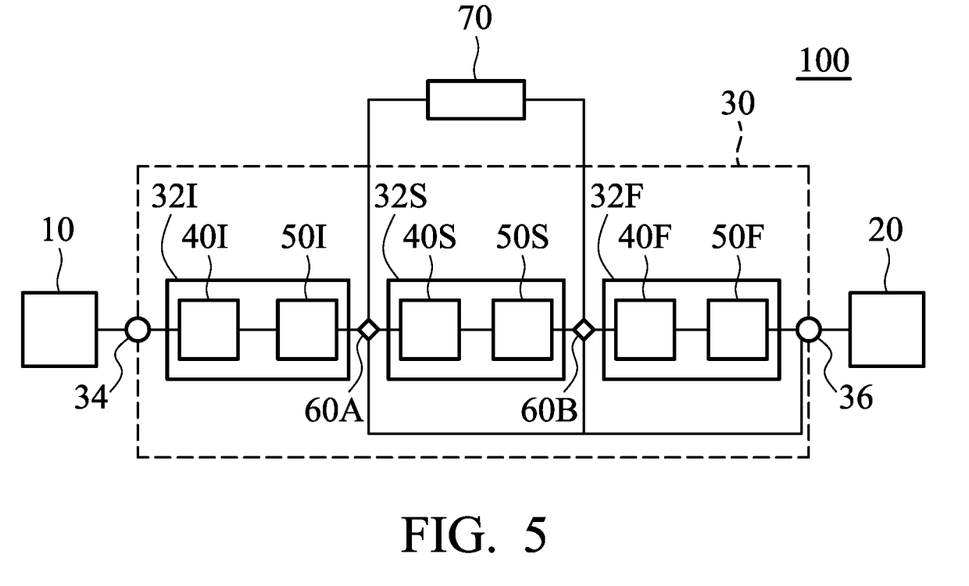
FIGS. 5-9 are schematic diagrams of the device for continuously manufacturing acrylate compound, which has a detection element and a control element, according to embodiments of the disclosure.

As shown in FIG. 5, the reaction system 30 has three reaction units (i.e. initial reaction unit 32I, second reaction unit 32S, and final reaction unit 32F). A first control element 60A is disposed between the initial reaction unit 32I and the second reaction unit 32S, wherein the centrifugal element of the previous reaction unit (i.e. the centrifugal element 501 of the initial reaction unit 32I) connects to the microreactor of the next reaction unit (i.e. the microreactor 40S of the second reaction unit 32S) via the first control element 60A. In addition, another first control element 60B is disposed between the second reaction unit 32S and the final reaction unit 32F, wherein the centrifugal element of the previous reaction unit (i.e. the centrifugal element 50S of the second reaction unit 32S) connects to the microreactor of the next reaction unit (i.e. the microreactor 40F of the final reaction unit 32F) via the first control element 60B.

As shown in FIG. 5, the device for continuously manufacturing acrylate compound of the disclosure 100 further includes a detection element 70 coupling to the first control element, wherein the alcohol compound conversion of the dehydration solution passing through the first control element is determined by the detection element.

In the case of the first control element 60B, the alcohol compound conversion of the dehydration solution supplied by the centrifugal element 50S and passing through the first control element 60B can be determined by the detection element 70. When the alcohol compound conversion determined by the detection element 70 is greater than or equal to a predetermined value (such as 60%-99%), the first control element 60B can introduce the dehydration solution supplied by the centrifugal element 50S into the collection tank 20 via the outlet port. As a result, the dehydration solution supplied by the centrifugal element 50S would not be introduced into the microreactor 40F of the final reaction unit 32F for further esterification, and the process for manufacturing acrylate compound may be terminated early since the required alcohol compound conversion of the dehydration solution is met. In addition, when the alcohol compound conversion determined by the detection element 70 is less than the predetermined value, the first control element 60B may introduce the dehydration solution supplied by the centrifugal element 50S into the microreactor 40F of the final reaction unit 32F in order to perform the esterification in the microreactor 40F and increase the whole alcohol compound conversion.

According to embodiments of the disclosure, the method for determining the alcohol compound conversion by the detection element 70 can be mass spectrometry (MS), high performance liquid chromatography (HPLC), gas chromatography (GC), or gas chromatography-mass spectrometry (GC-MS).

Figure 6:
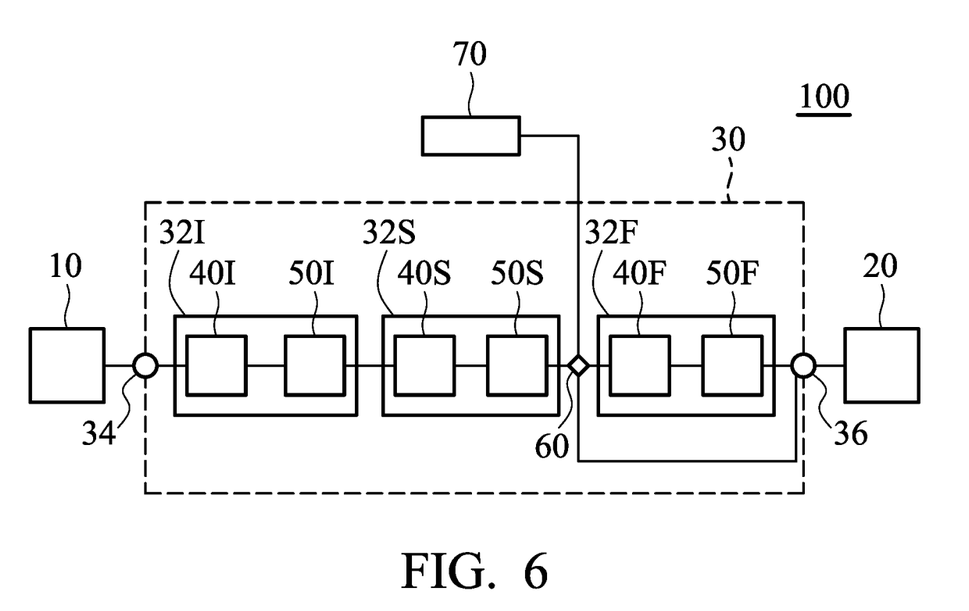

According to embodiments of the disclosure, the first control element is optionally disposed between two reaction units. For example, the first control element 60 can be merely disposed between the second reaction unit 32S and the final reaction unit 32F as shown in FIG. 6.

According to embodiments of the disclosure, in the device for continuously manufacturing acrylate compound of the disclosure, the reaction system can further include at least one second control element which is disposed in a reaction unit (called the current reaction unit), wherein the microreactor of the reaction unit connects to the centrifugal element in the same reaction unit via the second control element.

Figure 7:
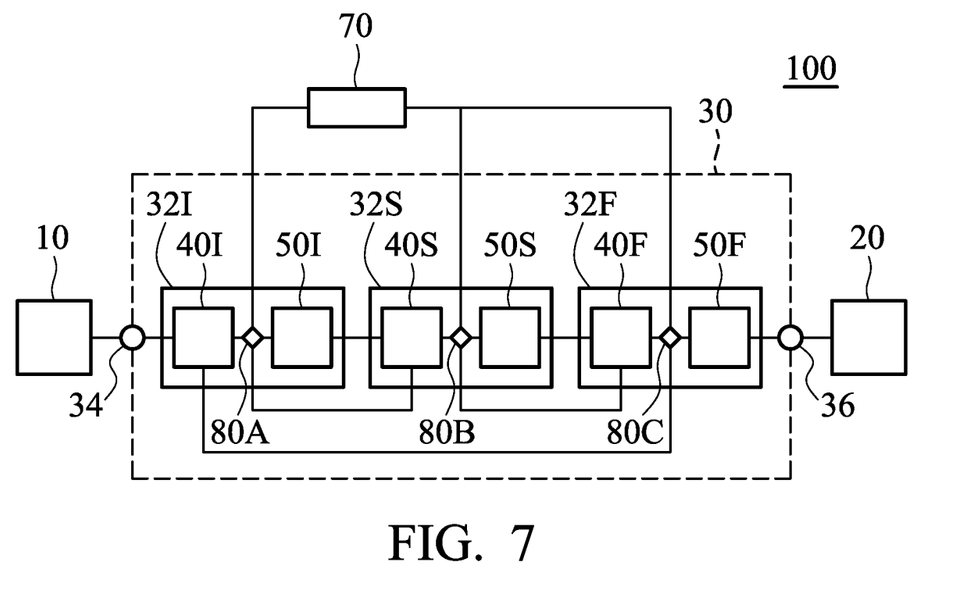
Figure 8:
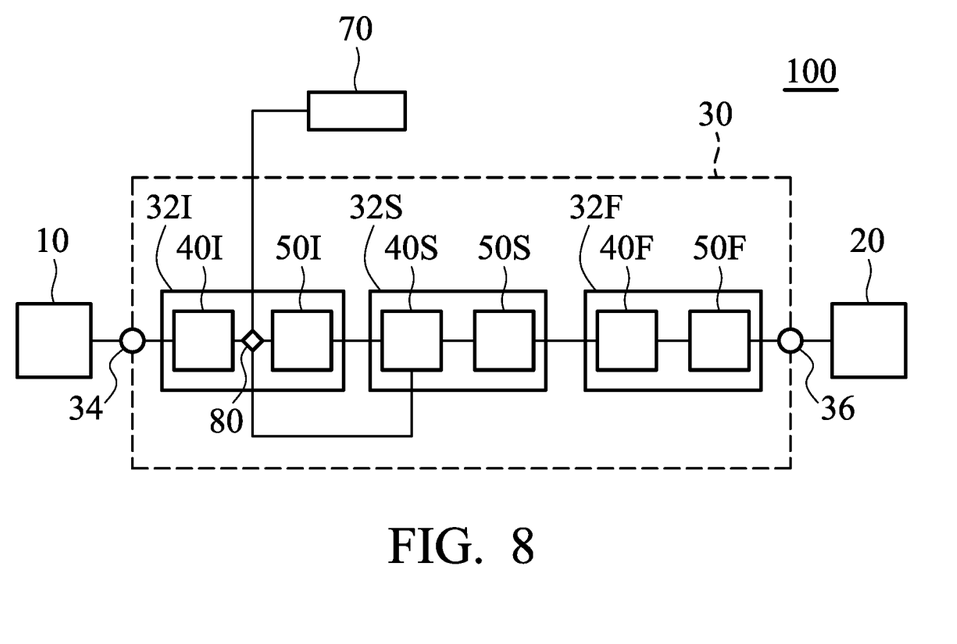

In addition, the acrylate-compound-containing solution supplied by the microreactor passes through the second control element before being introduced into a centrifugal element. As shown in FIG. 7, the reaction system 30 has three reaction units (i.e. initial reaction unit 32I, second reaction unit 32S, and final reaction unit 32F). A second control element 80A is disposed in the initial reaction unit 32I, and the microreactor 40I connects to the centrifugal element 50I via the second control element 80A; a second control element 80B is disposed in the second reaction unit 32S, and the microreactor 40S connects to the centrifugal element 50S via the second control element 80B; and, a second control element 80C is disposed in the initial reaction unit 32F, and the microreactor 40F connects to the centrifugal element 50F via the second control element 80C. As shown in FIG. 7, the alcohol compound conversion of the acrylate-compound-containing solution, which is supplied from the microreactor and passes through the second control element, can be determined by the detection element 70 coupling to the second control element 80A.

In the case of the first control element 80A, the alcohol compound conversion of the acrylate-compound-containing solution, which is supplied from the microreactor 40I and passes through the second control element 80A, is determined by the detection element 70. When the alcohol compound conversion determined by the detection element 70 is greater than or equal to a predetermined value (such as 12% to 60%), the second control element 80A introduces the acrylate-compound-containing solution into the centrifugal element 40S in the same reaction unit, thereby facilitating subsequent esterification. In addition, when the alcohol compound conversion determined by the detection element 70 is less than the predetermined value (i.e. the equilibrium of the esterification in the microreactor 40I is not achieved), the second control element 80A introduces the acrylate-compound-containing solution into the microreactor 40S of the next reaction unit (i.e. second reaction unit 32S) in order to perform esterification in the microreactor 40S without dehydration. As a result, a step of dehydration can be omitted, thereby accelerating the process.

According to embodiments of the disclosure, in the case of the second control element 80C disposed in the final reaction unit 32F, the alcohol compound conversion of the acrylate-compound-containing solution, which is supplied from the microreactor 40F and passes through the second control element 80C, is determined by the detection element 70. When the alcohol compound conversion determined by the detection element 70 is less than the predetermined value, the second control element 80C may introduce the acrylate-compound-containing solution supplied by the microreactor 40F into the microreactor 40I.

According to embodiments of the disclosure, the second control element can be optionally disposed in the reaction unit. According to embodiments of the disclosure, there is no second control element which is disposed in the final reaction unit. For example, the second control element 80 can be merely disposed in the initial reaction unit 32I, as shown in FIG. 7.

Figure 9:
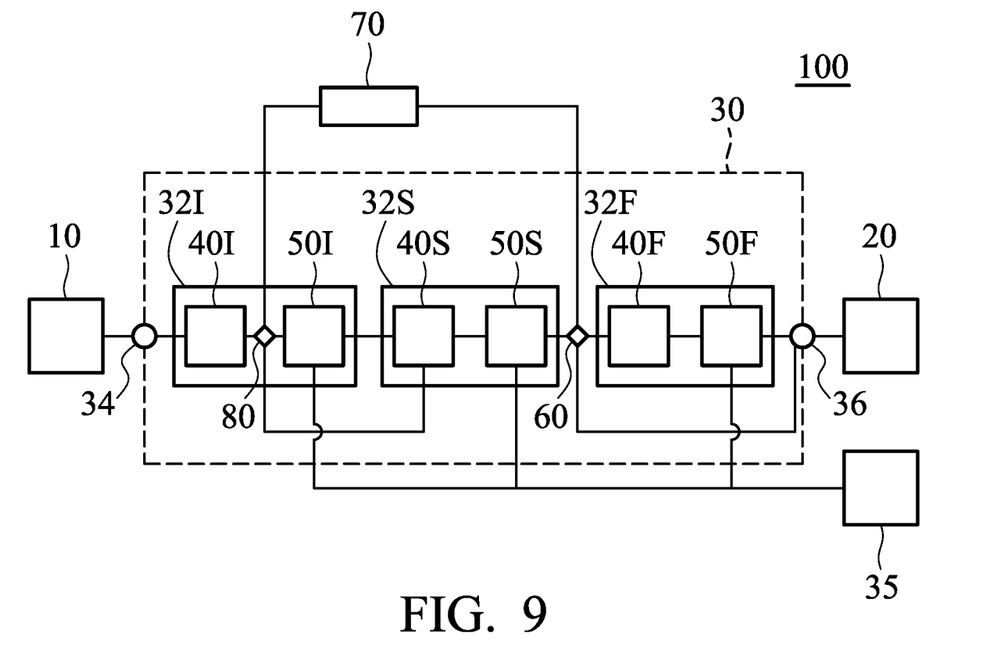

According to embodiments of the disclosure, in the device for continuously manufacturing acrylate compound of the disclosure, the reaction system can include the first control element, the second control element, and the detection element simultaneously. As shown in FIG. 9, the device for continuously manufacturing acrylate compound 100 can include a first control element 60 disposed between the second reaction unit 32S and the final reaction unit 32F; a the second control element 80 disposed in the initial reaction unit 32I; and a detection element 70. The detection element 70 is used to determine the alcohol compound conversion of the solution which passes through the first control element 60 and/or the second control element 80.

Figure 10:
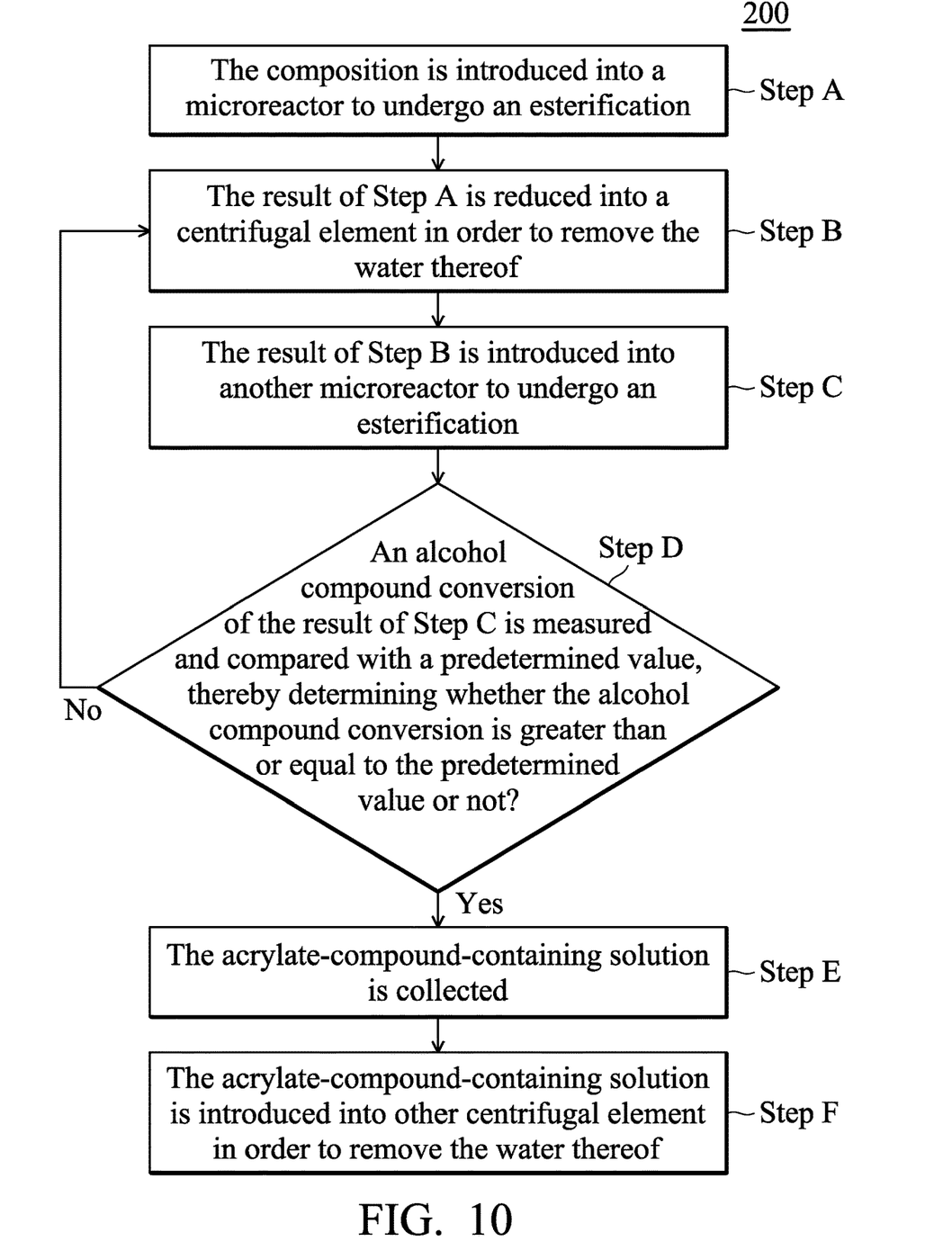
FIG. 10 is a flow chart illustrating a method for continuously manufacturing acrylate compound according to an embodiment of the disclosure.

According to embodiments of the disclosure, the disclosure also provides a method for continuously manufacturing acrylate compound. FIG. 10 is a flow chart illustrating a method 200 for continuously manufacturing acrylate compound according to an embodiment of the disclosure.

The method for continuously manufacturing acrylate compound of the disclosure includes the following steps. First, a composition is introduced into a microreactor to undergo esterification (Step A), wherein the composition includes an alcohol compound and an acrylic acid compound. Next, the result of Step A is reduced into a centrifugal element in order to remove the water of the result of the Step A (Step B). Next, the result of Step B is introduced into another microreactor to undergo esterification (Step C). Next, an alcohol compound conversion of the result of the step C is measured and then the obtained alcohol compound conversion is compared with a predetermined value (Step D). When the alcohol compound conversion is greater than or equal to the predetermined value, the acrylate-compound-containing solution (the result of Step C) is collected (Step E); In addition, when the alcohol compound conversion is less than the predetermined value, Steps B and C are repeated until the alcohol compound conversion is greater than or equal to the predetermined value, and then Step E is performed.

In some embodiments of the disclosure, after the Step E, the acrylate-compound-containing solution is introduced into other centrifugal element in order to remove the water of the result of Step E (Step F).

According to embodiments of the disclosure, the microreactors used in the steps A and all the steps C are different. Further, the centrifugal elements used in all the steps B are different.

According to embodiments of the disclosure, the method for continuously manufacturing acrylate compound can be a neat reaction. Therefore, the composition does not include organic solvent, azeotropic entrainer, or a combination thereof.

According to embodiments of the disclosure, the acrylic acid compound of the disclosure can have a structure represented by wherein R is hydrogen, methyl, ethyl, propyl, or isopropyl. According to embodiments of the disclosure, the acrylic acid compound of the disclosure is acrylic acid or methacrylic acid.

According to embodiments of the disclosure, the alcohol compound of the disclosure can be monohydric alcohol compound or polyol (such as a dihydric alcohol compound, trihydric alcohol compound, or tetrahydric alcohol compound). According to embodiments of the disclosure, the alcohol compound can be $C_{1-12}$ monohydric alcohol compound, $C_{1-12}$ dihydric alcohol compound, $C_{1-12}$ trihydric alcohol compound, or $C_{1-12}$ tetrahydric alcohol compound. According to embodiments of the disclosure, the alcohol compound can be monohydroxy alkanol. According to embodiments of the disclosure, the alcohol compound can be $C_{1-12}$ polyhydroxy alkanol. For example, the alcohol compound is methanol, ethanol, n-propanol, isopropanol, n-butanol, sec-butanol, tert-butanol, 2-ethylhexanol, methoxyethanol, ethoxyethanol, methoxymethanol, ethoxymethanol, ethylene glycol, propylene glycol, 1,3butanediol, 1,4-butanediol, 1,6-hexanediol, neopentyl glycol, 4-tert-butylcyclohexanol, 1,4-cyclohexanediol, 1,4-cyclohexanedimethanol, 2,2,4-trimethyl-1,3-pentanediol, 2-ethyl-2-methyl-1,3-propanediol, ditrimethylolpropane, diethylene glycol, triethylene glycol, tetraethylene glycol, dipropylene glycol, tripropylene glycol, or tetrapropylene glycol.

According to embodiments of the disclosure, in order to facilitate the esterification, the composition can further include a catalyst. The catalyst can be methanesulfonic acid, p-toluenesulfonic acid, or a combination thereof. According to embodiments of the disclosure, in order to avoid polymerization, the composition may further include a polymerization inhibitor. The polymerization inhibitor can be mono methyl ether hydroquinone, hydroquinone, dibutyl hydroxytoluene, or a combination thereof. The dose of the catalyst or polymerization inhibitor is not limited and can optionally be modified by a person of ordinary skill in the field.

According to embodiments of the disclosure, the alcohol compound is a monohydric alcohol compound, and the molar ratio of the alcohol compound to the acrylic acid compound is from 1 to 1.3. The alcohol compound is a dihydric alcohol compound, and the molar ratio of the alcohol compound to the acrylic acid compound is from 2 to 2.5. The alcohol compound is a trihydric alcohol compound, and the molar ratio of the alcohol compound to the acrylic acid compound is from 3 to 3.7. According to embodiments of the disclosure, the temperature of the microreactor can be maintained between 5° C. and 95° C.

According to embodiments of the disclosure, the acrylate compound of the disclosure can be a compound having at least one group represented by wherein R is hydrogen, methyl, ethyl, propyl, or isopropyl.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

0.28 g of mono methyl ether hydroquinone, 110.32 g of acrylic acid, 4.97 g of methanesulfonic acid, and 140 g of tripropylene glycol were mixed, obtaining a composition. The molar ratio of acrylic acid to tripropylene glycol is 2.1. Next, the composition was introduced into a first microreactor from a feed tank. The composition was stirred and reacted in the first microreactor at 90° C. for 4 hours. Next, the result was introduced into a centrifugal element from the first microreactor. After dehydration via the centrifugal element, the solution is introduced into a second microreactor. After stirring for 2 hours, the result was introduced into a collection tank from the second microreactor, obtaining tripropylene glycol diacrylate. Table 1 shows the conversion (determined by gas chromatography) after reacting for 4 hours (i.e. after the esterification in the first microreactor) and after reacting for 6 hours (i.e. after the esterification in the second microreactor). The result of nuclear magnetic resonance spectrometry of tripropylene glycol diacrylate of Example 1 is shown below: $^1$H NMR (CDCl$_3$, 400 MHz): δ6.43-6.38 (m, 2H), 6.20-6.11 (m, 2H), 5.90-5.80 (m, 2H), 5.15-3.43 (m, 9H), 1.81-1.17 (m, 9H).

Comparative Example 1

0.28 g of mono methyl ether hydroquinone, 110.32 g of acrylic acid, 4.97 g of methanesulfonic acid, and 140 g of tripropylene glycol were added into a reaction bottle. Next, after stirring and reacting at 90° C. for 6 hours, obtaining tripropylene glycol diacrylate. Table 1 shows the conversion (determined by gas chromatography) after reacting for 4 hours (i.e. after the esterification in the first microreactor) and after reacting for 6 hours (i.e. after the esterification in the second microreactor). Table 1 shows the conversion (determined by gas chromatography) after reacting for 4 hours and after reacting for 6 hours.

TABLE 1

| | conversion (%) after 4 hours | conversion (%) after 6 hours |
| --- | --- | --- |
| Example 1 | 48 | 65 |
| Comparative Example 1 | 45 | 51 |

As shown in Table 1, the conventional batch esterification (Comparative Example 1) exhibits a conversion of about 51% after reacting for 6 hours. The method for manufacturing acrylate compound employing the microreactor and the centrifugal element as disclosed in Example 1 exhibits a conversion of about 65% after reacting for 6 hours. Accordingly, the conversion of Example 1 is about 1.27 times larger than that of Comparative Example 1.

Although the disclosure has been described by way of example and in terms of the preferred embodiments, it should be understood that various modifications and similar arrangements (as would be apparent to those skilled in the art) can be made herein without departing from the spirit and scope of the disclosure as defined by the appended claims.

What is claimed is:

1. A device for continuously manufacturing acrylate compound, comprising:
   a reaction system, wherein the reaction system comprises at least two reaction units, an inlet port, and an outlet port, wherein each reaction unit comprises a microreactor and a centrifugal element;
   a feed tank, wherein the feed tank connects to the inlet port of the reaction system, in order to introduce an alcohol compound and acrylic acid compound into the reaction system; and
   a collection tank, wherein the collection tank connects to the outlet port of the reaction system, in order to collect the acrylate compound.

2. The device for continuously manufacturing acrylate compound as claimed in claim 1, wherein the at least two reaction units are connected in series.

3. The device for continuously manufacturing acrylate compound as claimed in claim 2, wherein the at least two reaction units comprise an initial reaction unit and a final reaction unit, and wherein the microreactor of the initial reaction unit connects to the inlet port of the reaction system, and the microreactor of the initial reaction unit connects to the inlet port of the reaction system.

4. The device for continuously manufacturing acrylate compound as claimed in claim 1, wherein the alcohol compound is reacted with the acrylic acid compound in the microreactor to undergo esterification.

5. The device for continuously manufacturing acrylate compound as claimed in claim 4, wherein the microreactor connects to the centrifugal element in the same reaction unit in order to introduce an acrylate-compound-containing solution into the centrifugal element.

6. The device for continuously manufacturing acrylate compound as claimed in claim 5, wherein the centrifugal element removes water from the acrylate-compound-containing solution, obtaining a dehydration solution.

7. The device for continuously manufacturing acrylate compound as claimed in claim 1, further comprising:
   a recovery tank, wherein the centrifugal element of the reaction unit connects to the recovery tank.

8. The device for continuously manufacturing acrylate compound as claimed in claim 2, wherein, in any two adjacent reaction units, the centrifugal element of a previous reaction unit connects to the microreactor of a next reaction unit.

9. The device for continuously manufacturing acrylate compound as claimed in claim 8, wherein the reaction system further comprises a first control element disposed between two adjacent reaction units, and wherein the centrifugal element of the previous reaction unit connects to the microreactor of the next reaction unit via the first control element, wherein the device for continuously manufacturing acrylate compound further comprises a detection element coupling to the first control element, and the alcohol compound conversion of the dehydration solution passing through the first control element is determined by the detection element.

10. The device for continuously manufacturing acrylate compound as claimed in claim 9, wherein when the alcohol compound conversion determined by the detection element is greater than or equal to a predetermined value, the first control element introduces the dehydration solution into the collection tank via the outlet port, and wherein when the alcohol compound conversion determined element introduces the dehydration solution into the microreactor of the next reaction unit.

11. The device for continuously manufacturing acrylate compound as claimed in claim 8, wherein the reaction system further comprises a second control element disposed in the reaction unit, and wherein the microreactor connects to the centrifugal element in the same reaction unit via the second control element, and wherein the device for continuously manufacturing acrylate compound further comprises a detection element coupling to the second control element, and the alcohol compound conversion of the acrylate-compound-containing solution, which is supplied from the microreactor and passes through the second control element, is determined by the detection element.

12. The device for continuously manufacturing acrylate compound as claimed in claim 11, wherein when the alcohol compound conversion determined by the detection element is greater than or equal to a predetermined value, the second control element introduces the acrylate-compound-containing solution into the centrifugal element in the same reaction unit, and wherein when the alcohol compound conversion determined by the detection element is less than a predetermined value, the second control element introduces the acrylate-compound-containing solution into the microreactor of the next reaction unit.

13. A method for continuously manufacturing acrylate compound, comprising:
   (A) providing a composition into a microreactor to undergo esterification, obtaining an acrylate-compound-containing solution with a first-stage alcohol compound conversion, and wherein the composition comprises an alcohol compound and an acrylic acid compound;
   (B) introducing the acrylate-compound-containing solution into a compound-containing solution, obtaining a dehydration solution; and
   (C) introducing the dehydration solution into another microreactor, obtaining an acrylate-compound-containing solution with a second-stage alcohol compound conversion.

14. The method for continuously manufacturing acrylate compound as claimed in claim 13, further comprising:
   (D) comparing the second-stage alcohol compound conversion with a predetermined value, and collecting the acrylate-compound-containing solution with the second-stage alcohol compound conversion when the second-stage alcohol compound conversion is greater than or equal to a predetermined value, or repeating step (B) and step (C) until obtaining an acrylate-compound-containing solution with a third-stage alcohol compound conversion when the second-stage alcohol compound conversion is less than the predetermined value, wherein the third-stage alcohol compound conversion is greater than or equal to the predetermined value.

15. The method for continuously manufacturing acrylate compound as claimed in claim 13, wherein the composition is free of an organic solvent, an azeotropic entrainer, or a combination thereof.

16. The method for continuously manufacturing acrylate compound as claimed in claim 13, wherein the alcohol compound is a monohydric alcohol compound, and the molar ratio of the alcohol compound to the acrylic acid compound is from 1 to 1.3.

17. The method for continuously manufacturing acrylate compound as compound, and the molar ratio of the alcohol compound to the acrylic acid compound is from 2 to 2.5.

18. The method for continuously manufacturing acrylate compound as claimed in claim 13, wherein the alcohol compound is a trihydric alcohol compound, and the molar ratio of the alcohol compound to the acrylic acid compound is from 3 to 3.7.

19. The method for continuously manufacturing acrylate compound as claimed in claim 13, wherein the composition further comprises a catalyst, and the catalyst is methanesulfonic acid, p-toluenesulfonic acid, or a combination thereof.

20. The method for continuously manufacturing acrylate compound as claimed in claim 13, wherein the composition comprises a polymerization inhibitor, and the polymerization inhibitor is mono methyl ether hydroquinone, hydroquinone, dibutyl hydroxytoluene, or a combination thereof.

* * * * *